(12) United States Patent
Libin et al.

(10) Patent No.: US 8,071,119 B2
(45) Date of Patent: Dec. 6, 2011

(54) CONTROLLED RELEASE IMPLANTABLE DISPENSING DEVICE AND METHOD (75) Inventors: Barry M. Libin, Great Neck, NY (US); Jeffrey M. Liebmann, Great Neck, NY (US); Weiliam Chen, Mt Sinai, NY (US)

(73) Assignee: Sustained Nano Systems LLC, Great Neck, NY (US)

( * ) Notice: Subject to any disclaimer, the term of this patent is extended or adjusted under 35 U.S.C. 154(b) by 30 days.

(21) Appl. No.: 12/386,853

(22) Filed: Apr. 23, 2009

(65) Prior Publication Data

US 2009/0270308 A1 Oct. 29, 2009

Related U.S. Application Data (63) Continuation-in-part of application No. 12/152,459, filed on May 14, 2008, which is a continuation-in-part of application No. 12/291,841, filed on Nov. 13, 2008.

(60) Provisional application No. 60/930,105, filed on May 14, 2007.

(51) Int. Cl.
*A61K 47/30* (2006.01)
*A61K 31/7088* (2006.01)
*A61K 38/00* (2006.01)

(52) U.S. Cl. ............ 424/427; 514/2; 514/44; 514/772.3

(58) Field of Classification Search ................. None
See application file for complete search history.

(56) References Cited

U.S. PATENT DOCUMENTS

| | | | |
|---|---|---|---|
| 4,343,789 A | 8/1982 | Kawata | |
| 4,478,818 A | 10/1984 | Shell et al. | |
| 4,713,244 A | 12/1987 | Bawa | |
| 5,725,869 A | 3/1998 | Lo | |
| 6,077,534 A | 6/2000 | Tobin | |
| 6,423,345 B2 | 7/2002 | Bernstein | |
| 6,630,486 B1 | 10/2003 | Royer | |
| 6,733,783 B2 | 5/2004 | Oshlack | |
| 6,869,976 B2 | 3/2005 | Royer | |
| 2002/0071870 A1* | 6/2002 | Sharma | 424/489 |
| 2002/0111603 A1* | 8/2002 | Cheikh | 604/891.1 |
| 2005/0037075 A1 | 2/2005 | Farokhzad | |
| 2005/0042290 A1 | 2/2005 | Kerc et al. | |
| 2005/0069580 A1 | 3/2005 | Hirsh | |
| 2005/0069591 A1 | 3/2005 | Bernstein | |
| 2008/0292680 A1 | 11/2008 | Libin et al. | |

FOREIGN PATENT DOCUMENTS

| | | |
|---|---|---|
| EP | 0 830129 | 3/1999 |
| EP | 0 941 071 | 9/1999 |
| WO | WO99/48519 | 9/1999 |
| WO | WO2004/050066 | 6/2004 |

OTHER PUBLICATIONS

Uchida et al., J. Pharm. & Pharmacol., 53:255-61 (2000).
Sadeghi et al., Drug Dev. & Ind. Pharm., 30:(7) 759-766 (2004).
Chiao et al., J. Microencapsulation, 11: (2) 161-170 (1994).
Davis et al., Crit. Rev. in Thera. Drug Carrier Systems, 19(4&5)385-423 (2002).
Frieberg et al., Int. J. of Pharmaceutics, 282:1-18 (2004).
Kanjickal et al., Crit. Rev. in Thera. Drug Carrier Systems,21(5):345-386 (2004).
Kausghal et al., Crit. Rev. in Thera. Drug Carrier Systems,21(3) 133-193 (2004).
Sethia et al., Crit. Rev. in Thera. Drug Carrier Systems, 20(2&3):215-2457 (2003).
Gratton et al. , The Effect of Particle Design on Cellular Internalization Pathways, Proc.Natl. Acad, Sci., (2008) www.pnas.org/content/105/33/11613/abstract.
Dinarvand, R. et al, Preparation of Biodegradable Microspheres and Matrix Devices Containing Naltrexone, AAPS Pharm Tech 2003; 4(3) Article 34, pp. 1-10.
PCT Search Report Dated Dec. 17, 2010.

* cited by examiner

*Primary Examiner* — Robert A Wax
*Assistant Examiner* — Danah Al-Awadi
(74) *Attorney, Agent, or Firm* — Hedman & Costigan, P.C.; James V. Costigan (57) ABSTRACT

A dispensing device having a polymer which is combined with a therapeutic agent in the form of a microparticle or nanoparticle which is "hyper-compressed" to form a controlled release dispensing device and methods of locally administering a therapeutic agent using said microparticles.

18 Claims, 7 Drawing Sheets

TABLE

Dexamethasone Level in Vitreous Humor

| Time | Concentration µg/ml |
|---|---|
| 6 hours | 1.134 |
| 24 hours | 1.462 |
| 3 days | 2.825 |
| 7 days | 1.596 |
| 14 days | 2.186 |

| Control | Concentration µg/ml |
|---|---|
| 24 hours | 1.195 |
| 3 days | 2.402 |
| 14 days | 1.885 |

Dexamethasone Level in Aqueous humor

| Time | Concentration ng/ml |
|---|---|
| 6 hours | 1381 |
| 24 hours | 491 |
| 3 days | 275 |
| 7 days | 365 |
| 14 days | 344 |

| Control | Concentration µg/ml |
|---|---|
| 24 hours | 293 |
| 3 days | 252 |
| 14 days | 0 detected |

CONTROLLED RELEASE IMPLANTABLE DISPENSING DEVICE AND METHOD

CROSS REFERENCE TO RELATED APPLICATIONS

This application is a continuation in part of Ser. No. 12/291,841, filed Nov. 13, 2009 which is a continuation in part of Ser. No. 12/152,459, filed May 14, 2008 which claims the priority of Ser. No. 60/930,105, filed May 14, 2007.

FIELD OF THE INVENTION

This invention relates to the field of controlled release implantable drug delivery devices.

BACKGROUND OF THE INVENTION

One of the major issues involving treatment involves the toxicity and/or adverse effects of pharmaceuticals that complicate the treatment of various conditions. Systemically administered medications tend to have effects that are undesirable when the therapeutic objective of the treatment is considered. If a pathology affects only a particular part or organ in the body, it is desirable to only administer treatment to that particular part or organ. In the prior art it has been known to provide localized radiation treatment by implanting radioactive pharmaceuticals in an organ that is to be treated so that radiation will be substantially confined to that organ. Most other implants have been intended to provide a systemic effect.

Two sustained delivery systems in the form of ophthalmic inserts that have been developed for commercial use are the Ocusert system (Akorn) and Lacrisert® (Aton). The Ocusert device is designed to provide for the release of medication at predetermined and predictable rates, which permits the elimination of frequent dosing by the patient, ensures nighttime medication, and provides a better means of patient compliance. The insert is elliptical with dimensions of 13.4 by 4.7 mm and 0.3 mm in thickness. The insert is flexible and is a multilayered structure consisting of a drug-containing core surrounded on each side by a layer of copolymer membranes through which the drug diffuses at a constant rate. The rate of drug diffusion is controlled by the polymer composition, the membrane thickness, and the solubility of the drug. The devices are sterile and do not contain preservatives. Ocusert inserts containing pilocarpine have been used in glaucoma therapy. After placement in the conjunctival fornix, the inserts are designed to release medication at the desired rates over a 7-day period at which time they are removed and replaced with new ones.

The Lacrisert® insert is a sterile, translucent, rod-shaped, water-soluble form of hydroxypropyl cellulose. The product is inserted into the inferior cul-de-sac of the eye of patients with dry eye states. The insert acts to stabilize and thicken the precorneal tear film and to delay its breakup. Inserts are typically placed in the eye once or twice daily. Following administration, the inserts soften and slowly dissolve.

The following U.S. patents disclose various ocular inserts for medicinal therapy. U.S. Pat. No. 4,730,013 to J. V. Bondi, et al., assigned to Merck & Company, Inc., discloses ocular inserts with or without pharmaceutically active agents, comprising 75% to 100% of a matrix of 15% polyvinyl alcohol, 10% glycerine, 75% hydroxy propyl methylcellulose phthalate, and 0-25% of a pharmacologically active agent. U.S. Pat. No. 5,637,085 describes the making of an implantable wafer for the treatment of solid cancer tumors.

U.S. Pat. No. 4,522,829 to Andreas Fuchs, et al., (Merck GmbH), discloses an intraocular pressure-lowering film insert of a 1-(p-2-iso-propoxyethoxy methyl-phenoxy)-3-isopropylamino-propan-2-ol or a physiologically acceptable salt thereof and an ophthalmically acceptable carrier.

U.S. Pat. No. 4,432,964 to Robert M. Gale (Alza Corp.) discloses an ocular insert for treating inflammation made of a pair of micronized steroids consisting of two topically acceptable different chemical therapeutic forms of betamethasone or a derivative, and a bio-erodible polymeric polyorthoester carrier.

U.S. Pat. No. 4,346,709 to Edward E. Schmitt (Alza Corp.) discloses an erodible device for delivering a drug to an environment of use, which includes a poly(orthoester) or a poly (orthocarbonate).

U.S. Pat. No. 4,303,637 to Robert M. Gale, et al., discloses an ocular insert composed of a beta U.S. Pat. No. 4,303,637 to Robert M. Gale, et al., discloses an ocular insert composed of a beta blocking drug in a polymer with the drug surrounded by the polymer selected from the group consisting of poly(olefin), poly(vinylolefin), poly (haloolefin), poly(styrene), poly(vinyl), poly(acrylate), poly (methacrylate), poly(oxide), poly(ester), poly(amide), and poly(carbonate).

U.S. Pat. No. 4,190,642 (Alza Corp.) discloses an ocular insert composed of a discrete depot of a pilocarpine solute and an epinephrine solute, a film of an ethylene-vinyl ester copolymer forming the insert, where fluid from the environment is imbibed through the wall into the depots to continually dissolve the solutes and release the formulation.

U.S. Pat. No. 4,093,709 to Nam S. Choi (Alza Corp.) discloses an ocular insert composed of an orthoester and an orthocarbonate polymer.

U.S. Pat. No. 3,993,071, issued Nov. 23, 1976 to Takeru Higuchi, et al., discloses a bio-erodible ocular insert for the controlled administration of a drug to the eye from 8 hours to 30 days, in which the drug formulation can also be microencapsulated and the microcapsules dispersed in the drug release rate controlling material.

U.S. Pat. No. 3,981,303 to Takeru Higuchi, et al. (Alza Corp.) discloses an ocular insert for the continuous controlled administration of a drug to the eye composed of a plurality of microcapsule reservoirs comprised of a drug formulation confined within a drug release rate controlling material, distributed throughout a bio-erodible matrix permeable to the passage of the drug at a higher rate than the rate of drug passage through the drug release rate controlling material, where the device is of an initial shape and size that is adapted for insertion and retention in the sac of the eye. The hydrophobic material may be selected from cholesterol, waxes, $C_{10}$ to $C_{20}$ fatty acids, and polyesters, and the drug may be selected from epinephrine, pilocarpine, hydrocortisone, idoxuridine, tetracycline, polymixin, gentamycin, neomycin, and dexamethasone.

U.S. Pat. No. 3,960,150 to Takeru Higuchi, et al. (Alza Corp.) discloses an ocular insert for the continuous controlled administration of a drug to the eye composed of a body of hydrophobic bio-erodible drug release rate controlling material containing a drug, where the body is of an initial shape adapted for insertion in the sac of the eye, where the drug release rate controlling material can be a polyester, and the drug may be selected from epinephrine, pilocarpine, hydrocortisone, idoxuridine, tetracycline, polymixin, U.S. Pat. No. 3,811,444, issued May 21, 1974 to Richard W. Baker, et al., assigned to the Alza Corp., discloses an ocular insert for the continuous controlled administration of a drug to the eye comprising a drug formulation dispersed through a body of selected hydrophobic polycarboxylic acid which erodes over time to dispense the desired amount of drug. The polycarboxylic acid can be a copolymer of an acid from the group of maleic acid, acrylic acid, lower alkyl acrylic acids from about 4 to about 6 carbon atoms, with a copolymerizable olefinically unsaturated material selected from the group consisting of ethylene, propylene, butadiene, isoprene and styrene and the lower alkyl vinyl ethers.

U.S. Pat. No. 3,630,200, issued Dec. 28, 1971, to Takeru Higuchi, assigned to the Alza Corporation, discloses a drug-dispensing ocular insert for insertion into the cul-de-sac of the conjunctiva between the sclera of the eyeball and the lid where the inner core contains the drug and is surrounded by a soft hydrophilic outer layer, where the outer layer can be composed of a polymer selected from the group consisting of hydrophilic hydrogel of an ester of acrylic or methacrylic acid, modified collagen, cross-linked hydrophilic polyether gel, cross-linked polyvinyl alcohol, and cross-linked partially hydrolyzed polyvinyl acetate and cellulosic gel. The inner core may be a polymer selected from the group of plasticized or unplasticized polyvinylchloride, plasticized nylon, unplasticized soft nylon, silicone rubber, polyethylene, hydrophilic hydrogel of an ester of acrylic or methacrylic acid, modified collagen, cross-linked hydrophilic polyether gel, cross-linked polyvinyl alcohol, cross-linked partially-hydrolyzed polyvinylacetate, cellulosic gel, ion-exchange resin and plasticized polyethylene terephthalate.

U.S. Pat. No. 3,618,604 to Richard A. Mess (Alza Corporation) discloses a drug-dispensing ocular insert adapted for insertion into the cul-de-sac of the eye, where the insert is a tablet containing a reservoir of drug formulation within a flexible polymeric material, and the polymeric material is formed of plasticized or unplasticized polyvinylchloride, plasticized nylon, unplasticized soft nylon, plasticized polyethylene terephthalate, silicon rubber, hydrophilic hydrogel of a ester of acrylic or methacrylic acid, modified collagen, cross-linked hydrophilic polyether gel, cross-linked polyvinyl alcohol, and cross-linked partially-hydrolyzed polyvinylacetate.

U.S. Pat. Nos. 3,993,071; 3,986,510; 3,981,303; 3,960,150, and 3,995,635 to Higuchi, et al., disclose a biodegradable ocular insert made from zinc alginate, poly(lactic acid), poly(vinyl alcohol), poly(anhydrides), and poly(glycolic acid).

A number of patents disclose the use of drug-loaded polyanhydrides (wherein the anhydride is in the backbone of the polymer) as matrix materials for ocular inserts. See, in general, U.S. Pat. Nos. 5,270,419; 5,240,963; and 5,137,728. Other U.S. patents that describe the use of polyanhydrides for controlled delivery of substances include: U.S. Pat. No. 4,857,311 to Domb and Langer, entitled "Polyanhydrides with Improved Hydrolytic Degradation Properties," which describes polyanhydrides with a uniform distribution of aliphatic and aromatic residues in the chain, prepared by polymerizing a dicarboxylic acid with an aromatic end and an aliphatic end); U.S. Pat. No. 4,888,176 to Langer, Domb, Laurencin, and Mathiowitz, entitled "Controlled Drug Delivery High Molecular Weight Polyanhydrides," which describes the preparation of high molecular weight polyanhydrides in combination with bioactive compounds for use in controlled delivery devices); and U.S. Pat. No. 4,789,724 to Domb and Langer, entitled "Preparation of Anhydride Copolymers," which describes the preparation of very pure anhydride copolymers of aromatic and aliphatic diacids.

U.S. Pat. No. 5,075,104 discloses an ophthalmic carboxyvinyl polymer gel for the treatment of dry eye syndrome.

U.S. Pat. No. 4,407,792 discloses an aqueous gel that includes a gel-forming amount of an ethylene-maleic anhydride polymer.

U.S. Pat. No. 4,248,855 discloses the salt of pilocarpine with a polymer containing acid groups for use as an ocular insert, among other things.

U.S. Pat. No. 4,180,064 and U.S. Pat. No. 4,014,987 disclose the use of poly(carboxylic acids) or their partially esterified derivatives as drug delivery devices. PCT/US90/07652 discloses that biologically active compounds containing a carboxylic acid group can be delivered in the form of an anhydride of a carrier molecule that modifies the properties of the molecule. U.S. Pat. No. 5,322,691 discloses the use of pressure to form drug containing ocular inserts from polymers with pressures up to 12 tons. The insets are made by mixing the drug powder with a polymer prior to compressing the mixture. There is no mention of the application of pressure to microspheres and polymers to form a dispensing device.

Although these patents disclose a number of types of ocular inserts, there is still a need to provide new dosage forms with modified properties for the delivery of local delivery of therapeutic agents. In particular, there is a need to provide a dispensing device that provides for the long acting local delivery of therapeutic agents to the eye and other locations in the body.

The formulations comprise a matrix of a polymer carrier and an active drug where the matrix is made by compression of micro or nano particles of a therapeutic agent in combination with a polymer. The matrix is positioned in or near the location where it will make available the therapeutic agent for treating or preventing pathologic conditions. The preferred polymeric matrix combines the characteristics of stability, strength, flexibility, low melting point, dispersability and suitable degradation profile. The matrix must retain its integrity for a suitable time so that it may be handled and placed in an aqueous environment, such as the eye, pancreas, liver, adrenal gland, colon, without loss of structural integrity. It should also be stable enough to be stored and shipped without loss of structural integrity. The matrix is designed to disintegrate into its constituent particles shortly after it is placed in position to release the therapeutic agent. Gliadel Implant Wafer (Eisai Corp. of N. Amer.) made of carmustine in polifeprosan intracranial implant wafer, is a white, dime-sized wafer made up of a biocompatible polymer that contains the cancer chemotherapeutic drug, carmustine (BCNU). After a neurosurgeon removes a high-grade malignant glioma, up to eight wafers can be implanted in the cavity where the tumor resided. Once implanted, Gliadel slowly dissolves, releasing high concentrations of BCNU into the tumor site. The specificity of Gliadel minimizes drug exposure to other areas of the body. Other recent products based on drug-loaded biodegradeable microspheres have reached the pharmaceutical marketplace. Drugs such as Lupron Depot (Abbott Laboratories), Trelstar Depot (Watson Pharmaceuticals) and Risperdal Consta (Ortho-McNeil-Janssen Pharmaceuticals) offer injectable parenteral drug delivery in depot formulations (IM or SC). Targeted local therapy include Bausch & Lomb's Retisert® a sterile nonbiodegradable implant that continuously delivers fluocinolone acetonide to the posterior segment of the eye.

U.S. Pat. No. 5,019,400 discloses a process for preparing microspheres using very cold temperatures to freeze polymer-biologically active agent mixtures into polymeric microspheres with very high retention of biological activity and material.

U.S. Pat. No. 6,183,781 discloses a process for fabricating implantable wafers produced by compression of: (1) polymer matrix fragments containing cryogenically pre-dispersed protein crystal produced by mechanical grinding, or (2) microcapsules produced by cryogenically suspending protein crystals in polymer solutions and coating them with a layer of polymer. The practical result of producing [polymer/protein crystal] fragments by mechanically grinding a cryogenically casted polymer-protein crystal slab is the formation of a highly heterogeneous mixture of polymer fragments, fractured protein crystal and protein crystal (full or partial) entrapped in polymer fragments. The microcapsule formation method described is a process to encapsulate either individual protein crystal or a cluster of protein crystals, which is analogous to coating protein crystals with a layer of polymer, followed by compression. In both cases, drug was not co-dissolved in the polymer solution to formulate microspheres or nanospheres with drugs uniformly dispersed/distributed inside the nano or microsphere matrices.

U.S. Pat. No. 7,462,366 discloses a process for preparing a drug delivery particle including a reservoir region having primarily large pores and a metering region. The particle can be highly spherical.

There remains a significant unmet need for dispensing devices that provide for the local delivery of long acting formulations of therapeutic agents. The applicants have devised formulations which comprise a matrix of a polymer carrier and an active drug where the matrix is made by hyper-compression of micro or nano particles of a therapeutic agent in combination with a polymer via modified high compression machines and/or dies. The matrix is positioned in the body in a location where it will be available for absorption to produce a substantially local effect. The preferred polymeric matrix combines the characteristics of stability, strength, flexibility, low melting point, dispersability and suitable degradation profile. The matrix must retain its integrity for a suitable time so that it may be handled and placed in an aqueous environment without loss of structural integrity. It should also be stable enough to be stored and shipped without loss of structural integrity. The matrix is designed to disintegrate into its constituent particles shortly after it is placed in position to release the therapeutic agent to the area where it will be available for therapeutic purposes.

SUMMARY OF THE INVENTION

The most significant objective in formulating small sized particles, i.e. microspheres or nanospheres for sustained delivery of pharmacologic agents is a controlled method for the continuous release of the (active) pharmacological substance over a prescribed period of time. It is known that, based on the size of the microsphere or nanosphere, a zero order release profile can be obtained through choice of a biocompatible, biodegradeable polymer matrix material, such as PLGA (poly D,L-lactic-co-glycolic acid). The properties of PLGA can be adjusted to the required delivery time by alteration of the polymer block ratios and the molecular weight to vary the rates of diffusion of the drug and the breakdown of the polymer. It has also been shown that loaded PLGA particles placed under "typical" compression forces (e.g. 37,000 psi) showed no change in shape to the particles or surface morphology. Furthermore, it has been shown that the release rate of drug with microparticles decreased the greater the concentration of microparticle versus nanoparticle content. Furthermore, it was shown that drug release from matrix tablets prepared with high nanoparticle content showed a biphasic pattern, with an immediate release, then no release, followed by further drug release (Murakami H. et al. J. of Controlled Release, Vol. 67, #1, 15 Jun. 2000 pp 29-36).

This invention utilizes "hyper-compression" forces on small size micro and nano particles (1 nm to 50 microns) to alter drug release profiles not shown by non-hyper-compressed particles. This includes utilizing carriers even with 100% microparticles, and altering the morphology of the particles themselves which increases the term of drug release. Hyper-compression goes beyond the selection of the polymer to affect release kinetics. Furthermore, this invention utilizes hyper-compression of small particles to minimize particle size, and increase drug concentration/unit volume. All of these changes in properties, including alteration of particle shape, results in extended controlled and consistent drug release profiles without a biphasic pattern.

The unit is compressed by a device that will provide sufficient force that the dosage form will be formed A machine such as the MTS 661 Series High Capacity Force Transducers are specifically designed for cyclic operation in through zero tension/compression and monotonic testing applications and available to measure tension and compression forces at maximum levels of 55,000 to 1,100,000 lb (250 to 5000 kN). The 661.2 Series Force Transducer was adapted to prepare the hyper-compressed delivery system through coupling it to the proper load cells and deployed in performing compression. Operation of the MTS tester was controlled by computer, and up to 500 kN of pressure could be applied for compression, with the resulting compressed unit shaped as desired, to be implanted or injected under the skin, e.g. subcutaneously or intramuscularly, or within the tissue of a specific bodily organ or structure, inhaled, taken orally or placed on the skin where it will continuously deliver a drug for local absorption.

The invention also includes a method of administering a therapeutic agent which comprises (a) forming a dosage form comprising a polymer in combination with an agent in the form of microparticles or nanoparticles; (b) hyper-compressing the microparticles or nanoparticles to form a controlled release dispensing unit; and (c) thereafter implanting or injecting said dispensing unit in a location in the body requiring localized treatment of a pathological condition with a therapeutic agent.

The invention also includes a method of administering a therapeutic agent, including antibiotics, proteins and other large molecules, through inhalation. While the invention may be used universally with any medicament that can be administered as a solid, it is particularly useful for the administration of small molecules such as synthetically derived organic compounds. An advantage in using the invention for systemic drug delivery via the pulmonary route, is by utilizing commonly used Nebulizers, metered dose inhalers (MDI's) and dry powder inhalers (DPI's) as a means of delivery.

Additionally, inhalation and subsequent absorption in the lung allows for more rapid onset of action compared to oral delivery methods, and avoids the possibility of first pass metabolism in the gastrointestinal tract. Furthermore, the lungs provide a large surface area and ready absorption, making it an excellent portal in using the invention for the pulmonary delivery of systemic drug therapies to treat chronic diseases such as diabetes and refractory conditions that require frequent drug administration for a protracted period of time, including the inhalation of nicotine as the therapeutic agent for smoking cessation. Other areas include agents for pain management, such as inhaled morphine or fentanyl for cancer pain, osteoporosis, migraine, sexual dysfunction, immunosuppression, premature ejaculation, growth hormone deficiency, neurological dysfunction, and cancer.

An additional advantage is using the invention for the local treatment of respiratory disease. This includes utilizing the invention for sustained delivery treatment of infections associated with severe respiratory diseases, including cystic fibrosis and bronchiectasis. This would include the use of antibacterials such as ciprofloxacin for the local treatment of chronic obstructive pulmonary disease (COPD). Other therapeutic agents would include anti-asthmatic drugs or pulmonary arterial hypertension. The invention allows for less frequent dosing, less drug concentrations, lower systemic blood levels to avoid microorganism resistance, the reduction or elimination of systemic side effects, and greater compliance.

Another advantage of the invention is its use with DPI's, which increasingly appear to be the inhalation route of choice: a) by avoiding the environmental and other problems of propellants; b) DPI's are simple to use; c) have a greater dose range than other devises, and d) provide advantages when formulating fragile molecules.

Another advantage of the invention is its significantly greater density per unit size, which enhance its flow properties and dispersion by a greater resistance to the forces of adhesion and cohesion that affect very fine low density powders, especially when ideal respirable size is less than 5 microns. Comparatively the density of a 5 micron particle of the invention particle would be equivalent to a non-hyper-compressed particle that is more than 7 microns in size, where the forces of adhesion are significantly less.

An additional advantage of the invention is less the lack of need for large particle sized excipient carriers or bulking agents, such as lactose, to be added to a DPI formulation to improve the inherent problem associated with highly cohesive fine particles: poor powder flow during capsule filling and metering, emptying, enhancing power stability, and poor aerosolization behavior resulting from the difficulties associate with deagglomeration.

The choice of excipients approved for this application is limited, with lactose used most commonly. This causes several major difficulties: 1) the effectiveness depends upon the respiratory breath being of sufficient energy to detach the active drug from the carrier for inhalation into the lung; this is a critical balance, and may be a problem with patients suffering from COPD; 2) the development of formulations that are carrier-free is important especially for relatively high-dose applications or those where there are chemical interactions between carrier and active ingredient, or for patients with carrier intolerance, a specific problem with lactose.

Capillary, van der Waals, and electrostatic forces are all important at this reduced particle size, with van der Waals dominant under most "normal" dry conditions. Thus, within a DPI system, it is important to consider carefully the cohesive forces between drug particles, the adhesive forces between device and drug, and the carrier/excipient and drug. As a result, carriers of relatively large particle size are often used to improve the flow characteristics of a DPI formulation.

The invention also includes a method of administering a therapeutic agent through transdermal and intra-epidermal delivery, which comprises (a) forming a dosage form comprising a polymer in combination with an agent in the form of nanoparticles or microparticles; (b) hyper-compressing the microparticles or nanoparticles to form a controlled release dispensing unit; and (c) thereafter placing the dispensing unit or modified dispensing unit into a transdermal patch for extended release of an active ingredient in the body requiring localized dermatologic or systemic treatment of a pathological condition. Transdermal or intra-epidermal absorption occurs through diffusion of the active agent, over time, resulting from the concentration gradient of the active through the dermis and, when desired, entering the capillary network.

The invention also includes a method of transdermal delivery affording a non-invasive or minimally invasive, easily-used method for delivering an active agent, to the skin or through the skin, to the general circulation. It helps to avoid compliance issues, eliminates partial first-pass inactivation by the liver, as well as irritation to the gastro-intestinal tract common to many oral agents.

Examples of currently marketed transdermal products include the nicotine patch, releasing nicotine over sixteen hours for the suppression of smoking; the scopolamine patch to prevent motion sickness for up to three days, a fentanyl patch, which provides pain relief for up to seventy-two hours, and a once a week estrogen-progestin contraceptive patch An additional advantage in using the invention is its ability to increase absorption through the superficial skin barrier, the stratum corneum. The stratum corneum consists of a keratinized surface of about ten microns in depth over most areas of the body. Typically, transdermal patches have been limited in drug administration to molecules capable of penetrating the corneum to access the underlying tissues and blood vessels for systemic distribution. Such molecules include hormones and other low molecular weight lipophilic molecules, such as nicotine or fentanyl which are effective at low doses. The largest daily dose of drug in patch form is that of nicotine (twenty-one milligrams).

There are also technologies (3M) which coat the active pharmaceutical agent on polycarbonate sharp microstructures, which when integrated onto an applicator patch system, can be forced into the skin to delivery the API to systemic circulation. One advantage is the limitation of accidental needle sticks.

The advantage of the present invention is that the microstructures themselves are formed of hyper-compressed nanoparticles whose size and shape allow enhanced diffusion of the API through skin. Thus, the dosage formulation of an active agent, such as nicotine, in a hyper-compressed microcapsule formulation is prepared by first co-dissolving 100 mg. of nicotine with 900 mg of poly(dl-lactide) polymer (PLA, intrinsic viscosity 0.66-0.80 dl/g, (as measured in a Ubbelholde viscometer by assessing the flow time of a 1.0 g polymer solution) in 50 ml of chloroform at 25°. The nicotine/PLA solution is dispersed into 200 ml of a 4% polyvinyl alcohol (30K to 70K MW) solution. The nicotine/PLA/chloroform solution is dispersed in the PVA solution by sonication (with a probe ultra-sonicator) while maintained at 4° C.; a nanoemulsion is produced after 15 minutes of sonication. This nanoemulsion is agitated by an impeller rotating at 700 RPM overnight to allow chloroform to evaporate. The nanospheres formed are less than 500 nanometers in size and are recovered by high-speed centrifugation, washed 3 times and lyophilized. These nanospheres also form a free flowing powdery bulk material and could be hyper-compressed to form pellets. For local and systemic delivery, 250 mg of the microspheres are placed, for example, in an 8 mm diameter stainless steel mold and a hyper-compression force of 200,000 psi is used to form a dispensing device which contains up to 25 mg of nicotine. The controlled release dispensing device unit can be of any size or shape as dictated by need, and through modification of the compressing molds.

An additional advantage in using the invention is where there is a need its ability to increase systemic absorption through the stratum corneum. The invention includes an intradermal dispensing device being formed in a lower mold that forms, on one side, sharp "drug delivery microporates," extending from the body of the dispensing device. The upper and lower stainless steel molds are similar to the mold described to make the hyper-compressed particles of the invention (see example 1, below), with the addition of hollowed out channels or 'holes' formed by dies or drills, and placed through the superior or upper surface of the bottom mold in a random or systematic pattern. The channels or holes are pyramidal or cone like in shape, with an inner diameter at its superior or top end of a 0.1-0.5 mm range, and narrowing to an apical point with a dimension similar to an 27-33 gauge needle, with a length of from 0.05 mm to 1.0 mm, depending upon anatomical need. The channels may be spaced between 0.25 to 5 mm apart, depending upon size and need, so that a 10 mm by 10 mm controlled release dispensing unit may have 100 or more such channels placed into it, depending upon needed concentration. When the polymer and active are compressed under hyper-compressed conditions, the upper, flat surfaced mold forces or compresses the particles into the lower 'channeled' mold, resulting in a controlled release dispensing unit composed of drug laden pyramidal, or conelike 'drug delivery microporate' shaped pointed extensions. The term "microporate" is used to describe a hyper-compressed cone-like dosage form that ends in a point, able to penetrate or 'porate' the stratum corneum, The purpose of the 'microporates' are to aid in the active agent gaining access through the stratum corneum to the interdermal tissues, and greater access to the blood vessels for systemic circulation. The "microporates" may also be designed to "break" and remain beneath the skin with a sustained delivery of the active agent into the dermis for weeks or months. Within minutes after application the patch may be removed.

Microporate Modified Controlled Release Dispensing Unit

An additional advantage of the invention is the placing of the controlled release dispensing unit directly on the adhesive layer of the patch, with the "porate" side facing the skin side. The structure of a typical patch, as oriented to the skin, is as follows:

Film Backing soft skin toned packet cover upon which finger pressure is placed;
Drug/Adhesive Layer contains 'microporate' dispensing unit on adhesive layer
Protective Liner—removed by patient
Skin The patch consists of a superficial impermeable backing made of polyester film, ethylene vinyl alcohol copolymer (EVA), or polyurethane film, an adhesive, generally an acrylic polymer with polyisobutylene or other such chemical, which holds the patch in place on the skin and which contains the delivery system, and a protective cover that is peeled away before applying the patch, which covers and is thick enough to protect the punctuate ends. The protective liner, composed of polyester fabric, is removed before applying, similar to a Band-Aid, and if systemic absorption is desired, thumb pressure is applied until the thumb meets the resistance of the underlying skin, to allow the active "microporates" on the adhesive layer to penetrate the outer surface of the skin. The active can be dispensed for a period of minutes, or hours or days or weeks before the patch is removed. Once within the interstitial tissue, the drug forms a reservoir from which it is slowly released into the blood vessels for systemic delivery or into the diseased cells, as in skin cancer or other pathology.

The physicochemical parameters influencing particles crossing through the epithelial barrier are affected by the size and shape of the particles, as previously described. The use of nanoparticles to cross the epithelial barrier in drug delivery has not been utilized significantly. Gaumet et al, *Localization and quantification of biodegradable particles in an intestinal cell model: the influence of particle size*. Gaumet M, Gurny R, Delie F. Eur J Pharm Sci. 2009 Mar. 2; 36(4-5):465-73. Epub 2008 Dec. 11) has shown the influence of the size of well characterized biodegradable polymeric particles on cellular uptake by Caco-2 cells. Poly (d,l-lactide-co-glycolide acid) (PLGA) particles loaded with a fluorescent dye, 3,3'-dioctadecyloxacarbo-cyanine perchlorate (DiO), were prepared by the emulsion evaporation process. Five batches of particles with narrow size distribution (100, 300, 600, 1000, and 2000 nm) were produced using selective centrifugation. Surface properties (zeta potential, hydrophobicity and residual surfactant rate) were similar among all batches. The interaction was clearly dependant on particle size and concentration. Particles in the range of 100 nm presented a higher interaction when compared to larger particles. Cellular localization of particles by confocal microscopy showed the association of the poly (d,l-lactide-co-glycolide acid) particles with the cells. Small particles were observed intracellularly, whereas particles larger than 300 nm were associated with the apical membranes. Some of the 100 nm PLGA particles were localized in the nuclei of the cells.

The invention also includes a method of providing a controlled sustained release solid dosage tablet form to administer a therapeutic agent through oral delivery. Oral controlled release dosage forms have shown therapeutic advantages over those not having controlled release, including: reduction in dosing frequency, reduced fluctuation in circulating drug levels, increased patient compliance, and more uniform pharmacologic response. Oral controlled release can be achieved in several ways, one of which is in the form of gastroretentive dosage forms, those that can be retained in the stomach or upper part of the intestine. Such drugs include metformin, cirpofloxacin, levodopa, etc. It is widely acknowledged that the extent of gastrointestinal tract drug absorption is related to contact time with the small intestinal mucosa. The invention comprises (a) forming a dosage form comprising a polymer in combination with an agent in the form of microparticles or nanoparticles; (b) hyper-compressing the microparticles or nanoparticles to form a controlled release dispensing unit; and (c) thereafter placing the dispensing unit in a hyper-compressed tablet, as described above. A coating may be applied to hide the taste of the tablet's components, to make the tablet smoother and easier to swallow, and to make it more resistant to the environment, extending its shelf life. A tablet can be formulated to deliver an accurate dosage to a specific site; it is usually taken orally, but can be administered sublingually, rectally or intravaginally. It consists of an active pharmaceutical ingredient (A.P.I.) with biologically inert excipients in a hyper-compressed, solid form.

Accordingly, it is an object of the invention to provide a dispensing device for use as an implantable or injectable controlled release device for the local treatment of a pathological condition with therapeutic agent(s) over a period of time.

It is also an object of this invention to improve patient compliance with physician directed administration of therapeutic agents by minimizing the number of doses and maximizing the local effect of a therapeutic effect from a specific dose.

It is therefore an object of the present invention to provide a method for the localized treatment of pathologic conditions using a matrix that is made by hyper-compressing units of microparticles or nanoparticles that comprise a therapeutically compatible polymer and a therapeutic agent.

It is also an object of the invention to provide a dispensing device that is made by hyper-compressing microparticles or nanoparticles containing a therapeutic agent with a compressed polymer which will release a therapeutic agent over an extended period of time, in a smooth, uniphase, consistent release pattern.

It is also an object of the invention to provide hydrophilic or preferably, hydrophobic drugs for ophthalmic pathologies or other types of pathology, including antibacterials, antibiotics, anti-inflammatory agents, immunosuppressive agents, anti-glaucoma agents etc.

It is also an object of this invention to avoid active patient involvement with the administration of a therapeutic agent by having a physician place a dispensing device in a position where it will locally deliver the therapeutic agent over an extended period of time without any action on the part of the patient.

It is also an object of this invention to provide a dispensing device that will provide local controlled release of a therapeutic agent from a non-toxic biodegradable polymer system that does not have to be removed from the body after exhaustion of a therapeutic agent It is also an object of the invention to provide a method of locally administering a drug which comprises forming a dispensing device comprising a polymer in combination with a therapeutic agent in the form of a microparticle or nanoparticle which is hypercompressed to form a controlled release dispensing unit and thereafter placing said controlled release dispensing unit in contact with an injectable liquid to disperse the microparticles and form a suspension of microparticles prior to placing said suspension in a patient in a location that will provide for release of the drug.

It is also an object of the invention to form the hyper-compressed microparticles into a dry powder for inhalation administration.

These and other objects of the invention will become apparent from a review of the present specification.

DETAILED DESCRIPTION OF THE INVENTION

The dispensing device of the invention comprises a polymer that is combined with a therapeutic agent and hyper-compressed to form a controlled release dispensing unit. The therapeutic agents that may be mixed with the polymer comprise hydrophilic or preferably, hydrophobic drugs that are antifungal, antibacterial, antibiotic, anti- The dispensing device of the invention comprises a polymer that is combined with a therapeutic agent and hyper-compressed to form a controlled release dispensing unit. The therapeutic agents that may be mixed with the polymer comprise hydrophilic or preferably, hydrophobic drugs that are antifungal, antibacterial, antibiotic, anti-inflammatory, immunosuppressive, tissue growth factors, dentinal desensitizers, antioxidants, nutritional agents, vitamins, odor masking agents for example. Specific examples include steroids, non-steroidal anti-inflammatory drugs, antihistamines, antibiotics, mydriatics, beta-adrenergic antagonists, anesthetics, alpha-2-beta adrenergic agonists, mast cell stabilizers, prostaglandin analogues, sympathomimetics, parasympathomimetics, antiproliferative agents, agents to reduce angiogenesis and neovascularization, vasoconstrictors and combinations thereof and any other agents designed to treat disease such as a anti-neoplastic agent, a polynucleotide, or a recombinant protein analog, an angiogenic inhibitor such as Endostatin, or thalidomide; 5-fluorouracil, paclitaxol, minocycline, timolol hemihydrate, rhHGH, bleomycin, ganciclovir, huperzine, tamoxifen, piroxicam, levonorgesterel, cyclosporin and the like. Other agents include but are not limited to particular steroids but include steroids such as prednisone, methylprednisolone, dexamthasone; antibiotics including neomycin, tobramycin, aminoglycosides, fluoroquinolones, polymyxin, sulfacetamide, agents such as pilocarpine, isopilocarpine, physostigmine, demecarium, ecothiphate and acetyl choline and salts thereof; mydriatics and cycloplegics including agents such as atropine, phenylephrine, hydroxyamphetamine, cyclopentolate, homatropine, scopolamine, tropicamide and salts thereof; anesthetics include, lidocaine, proparacaine, tetracaine, phenacaine, and the like; beta-blockers such as timolol, carteolol, betaxolol, nadolol, levobunolol, carbonic anhydrase inhibitors such as dorzolamide, acetozolamide, prostaglandin analogues such as latanoprost, unoprostone, bimatoprost or travoprost.

The polymer that is used in combination with the therapeutic agent is a pharmaceutically acceptable polymer that is non-toxic and non-irritating to human tissues. These polymers include monomeric and co-polymeric materials. The preferred polymers comprise a biocompatible and biodegradable polymer that, prior to hyper-compression may be formed into microparticles known as microspheres or microcapsules which are typically in the size range of about 2 microns to about 50 microns, preferably from about 2 to about 25 microns and more preferably from about 5 to about 20 microns in diameter. The term microsphere is used to describe a substantially homogeneous structure that is obtained by mixing an active drug with suitable solvents and polymers so that the finished product comprises a drug dispersed evenly in a polymer matrix which is shaped as a microsphere. Depending on the selected size range of the microparticles the term nanoparticle is used to describe structures sized from 1 to 1000 nanometers. A nanometer (nm) is one billionth of a meter or about the size of 10 hydrogen atoms. Currently, nanoparticle drug carriers mainly consist of solid biodegradable particles ranging from 50-300 nm in size. Generally a particle size should be selected so that the particles may be easily measured and transferred as necessary for the purpose of placing the particle in a suitable press for the application of hyper-compressive forces to form the compressed dosage form. The compressed particles are designated as the matrix which when placed in water or in contact with aqueous body fluids, such as the dermis, lung or intestine, will cause the compressed particles to disaggregate and form into the separate particles that were compressed to form the matrix.

An additional aspect of the invention is that once these microspheres and nanospheres are hyper-compressed, they result in an altered or distorted particle shape ranging in variation of degrees of elongation, circularity, and convexity or surface roughness that results from the application of hyper-compressive forces. Such distorted shapes appear to alter particle activity (Gratton S E A, DeSimone J M et al. Proc of the Nat Acad of Sci 2008); Mitragoti S et al. Proc Nat Acad of Sci 2008). It is not known why the hyper-compression alters the activity of the microspheres and nanospheres but without being bound by any theory of operation, the inventors believe 1) the hyper-compression has an effect because the drug is more concentrated on a weight volume basis in comparison to uncompressed microspheres or nanospheres, and 2) the change in shape of the particles also appears to have an the effect on a given dose of a drug by reducing the rate of release of drug from the hyper-compressed dosage form, and 3) by enhancing the uptake of a drug or active agent on a cellular level.

The hyper-compressed particles can be re-dispersed in a suitable aqueous vehicle for injection. Sterile normal saline or other isotonic solutions may be used for this purpose. Since the particle size of the hyper-compressed individual microspheres has been reduced, substantially more drug can be delivered using the same volume of microspheres. Nanoparticles may be formed, for example, by sonicating a solution of polylactide polymer in chloroform containing a 2% w/w solution of polyvinyl alcohol in the presence of a therapeutic agent such as an ophthalmic therapeutic agent for 10 minutes, using a ultasonicator (Misonix XL-2020 at 50-55W power output. Thereafter, the emulsion is stirred overnight at 4° C. to evaporate the chloroform and obtain nanoparticles of the polymer and the therapeutic agent. The medicated nanoparticles can easily access the interior of a living cell and afford the unusual opportunity of enhancing local drug therapy.

Microcapsules may also be used to form the compressed dosage forms of the invention. The term microcapsule is used to describe a dosage form, which is preferably non-spherical and has a polymer shell disposed around a core that contains the active drug and any added excipient which is in the size range set forth above. Generally microcapsules may be made by using one of the following techniques:
(1) phase separation methods including aqueous and organic phase separation processes, melt dispersion and spray drying;
(2) interfacial reactions including interfacial polymerization, in situ polymerization and chemical vapor depositions;
(3) physical methods, including fluidized bed spray coating; electrostatic coating and physical vapor deposition; and
(4) solvent evaporation methods or using emulsions with an anti-solvent.

In general, the microparticles are comprised of from about 0.00001 to about 50 parts by weight of therapeutic agent and is further comprised of from about 50 to about 99.99999 parts by weight of polymer per 100 parts by weight of the total weight of therapeutic agent and polymer. The preferred ranges are from 1 to 50, 5 to 40, and 20 to 30 parts by weight of therapeutic agent, the balance comprised of polymer. If desired, from 1 to 5 wt % of a binder, such as polyvinyl pyrrolidone, may be homogeneously mixed with the microparticles prior to the compression step.

The amount of drug that is implanted may vary but generally from 0.5-20% of the usual oral or intravenous dose of the drug may be employed but may vary substantially depending on the solubility, the area of implantation, the patient and the condition to be treated. Microspheres may be formed by a typical in-emulsion-solvent-evaporation technique as described herein.

In order to provide a biodegradable polymeric matrix for a controlled release dosage form which is suitable for placement in a position where a therapeutic agent may be released for treatment of a pathology, it is preferable to select the polymer from poly(alpha hydroxy butyric acid), poly(p-dioxanone) poly(l-lactide), poly(dl-lactide), polyglycolide, poly(glycolide-co-lactide), poly(glycolide-co-dl-lactide), a block polymer of polyglycolide, trimethylene carbonate and polyethylene oxide, or a mixture of any of the foregoing. The synthetic polymer may be a polylactide or a poly(lactide-co-glycolide) with any MW (weight average) or MW polydispersity, all ratios between lactic acid (LA) and glycolic acid (GA), and all degrees of crystallinity. Generally, the MW ranges from about 500 to about 10,000,000 Da, preferably from about 2,000 to about 1,000,000 Da, and more preferably from about 500 to about 5,000 Da. The p(LGA) with the ratio of LA:GA at about 75:25 to about 85:15 (mol:mol) and the MW from about 5,000 to about 500,000 may be used. The lactide/glycolide polymers are bulk-eroding polymers (not surface eroding polymers) and the polymer will hydrolyze when formed into a microparticle matrix as water enters the matrix and the polymer decreases in molecular weight. It is possible to shift the resorption curves to longer times by increasing the polymer molecular weight, using L-polymers and decreasing the surface area by increasing the size of the microparticles or the size of the dosage form. The lactide/glycolide copolymers are available with inherent viscosities as high as 6.5 dl/g and as low as 0.15 dl/g. The lower molecular weight copolymers are preferred for the present invention. It has been found that a mol ratio of 50:50 of glycolide to lactide results in the most rapid degradation and the corresponding release of drug. By increasing the ratio of lactide in the polymer backbone from about 50 mole % to 100% the rate of release can be reduced to provide an extended therapeutic effect from a single dosage unit.

A preferred encapsulating polymer is poly(glycolide-co-dl-lactide), which serves as the preferred controlled release delivery system for the dispensing device is similar in structure to the absorbable polyglycolic acid and polyglycolic/polylactic acid suture materials. The polymeric carrier serves as a sustained-release delivery system for the therapeutic agents. The polymers undergo biodegradation through a process whereby their ester bonds are hydrolyzed to form normal metabolic compounds, lactic acid and glycolic acid and allow for release of the therapeutic agent.

Copolymers consisting of various ratios of lactic and glycolic acids have been studied for differences in rates of degradation. It is known that the biodegradation rate depends on the ratio of lactic acid to glycolic acid in the copolymer, and the 50:50 copolymer degrades most rapidly. The selection of a biodegradable polymer system avoids the necessity of removing an exhausted non-biodegradable structure from the eye with the accompanying trauma.

After the microspheres are prepared, they are compressed at very high forces to form the dispensing device of the invention. The hyper-compression may be carried out in an apparatus that is capable or permits the application of from 150,000 to 600,000 psi (hereafter K is used in place of 1,000) pressure to microparticles or nanoparticles, and more preferably from 175K psi to 550K psi and especially 220K psi. to 500K psi, and especially 200K psi to 400K psi) The term psi (pounds per square inch) is determined by taking the force in pounds that is applied to the particular dosage form and measuring or calculating the area of the top of the dosage form in square inches so that a conversion may be made to express the pressure applied to the dosage form in psi. The hyper-compressed dispensing device may be a perfect spheroid, but preferably a distorted spheroid such as a flat disc, rod, pellet with rounded or smooth edges that is small enough to be placed under the skin in a location such as bones and their joints, including the knuckles, toes, knees, hips and shoulders; glands, e.g. pituitary, thyroid, prostate, ovary or pancreas, or organs, e.g. liver, brain, heart, and kidney. More particularly, the dispensing device of the invention may be utilized to treat pathology by implanting the device at or near the site of the pathology, or in a way that will affect the pathology, such as any part that comprises the body of a human or animal or fish or other living species. Such parts may include the contents of a cell, any part of the head, neck, back, thorax, abdomen, perineum, upper or lower extremities. Any part of the osteology including but not limited to the vertebral column, the skull, the thorax, including the sternum or ribs, the facial bones, the bones of the upper extremity, such as the clavicle, scapula or humerus; the bones of the hand, such as the carpus; the bones of the lower extremity, such as the ilium or the femur; the foot, such as the tarsus; joints or ligaments; muscles and fasciae; the cardiovascular system, such as the heart, the arteries, the veins, or the capillaries or blood; the lymphatic system, such as the thoracic duct, thymus or spleen; the central or peripheral nervous system, the sensory organs, such as eye, ear, nose; the skin; the respiratory system, such as the lungs, the larynx, the trachea and bronchi; the digestive system, such as the esophagus, the stomach or the liver; the urogenital system, such as the urinary bladder, the prostate, or the ovary; the endocrine glands, such as the thyroid, the parathyroid or the adrenals.

It is contemplated that the insertion of the dispensing device such as in the form of an implant or an injectable liquid suspension, according to the invention, will be carried out by a physician, dentist, veterinarian, nurse, or other trained professional, as it is contemplated that the method of insertion may involve procedures well known to a trained professional in order that the device will be properly placed. The (injectable) dispensing device may be implanted by use of a modified syringe that will have a barrel provide with a plunger element that will extrude the dispensing device of the invention. Such a device is shown in U.S. Pat. No. 5,236,355 and FIG. 1 of that patent is incorporated by reference into the present application.

Figure 5:
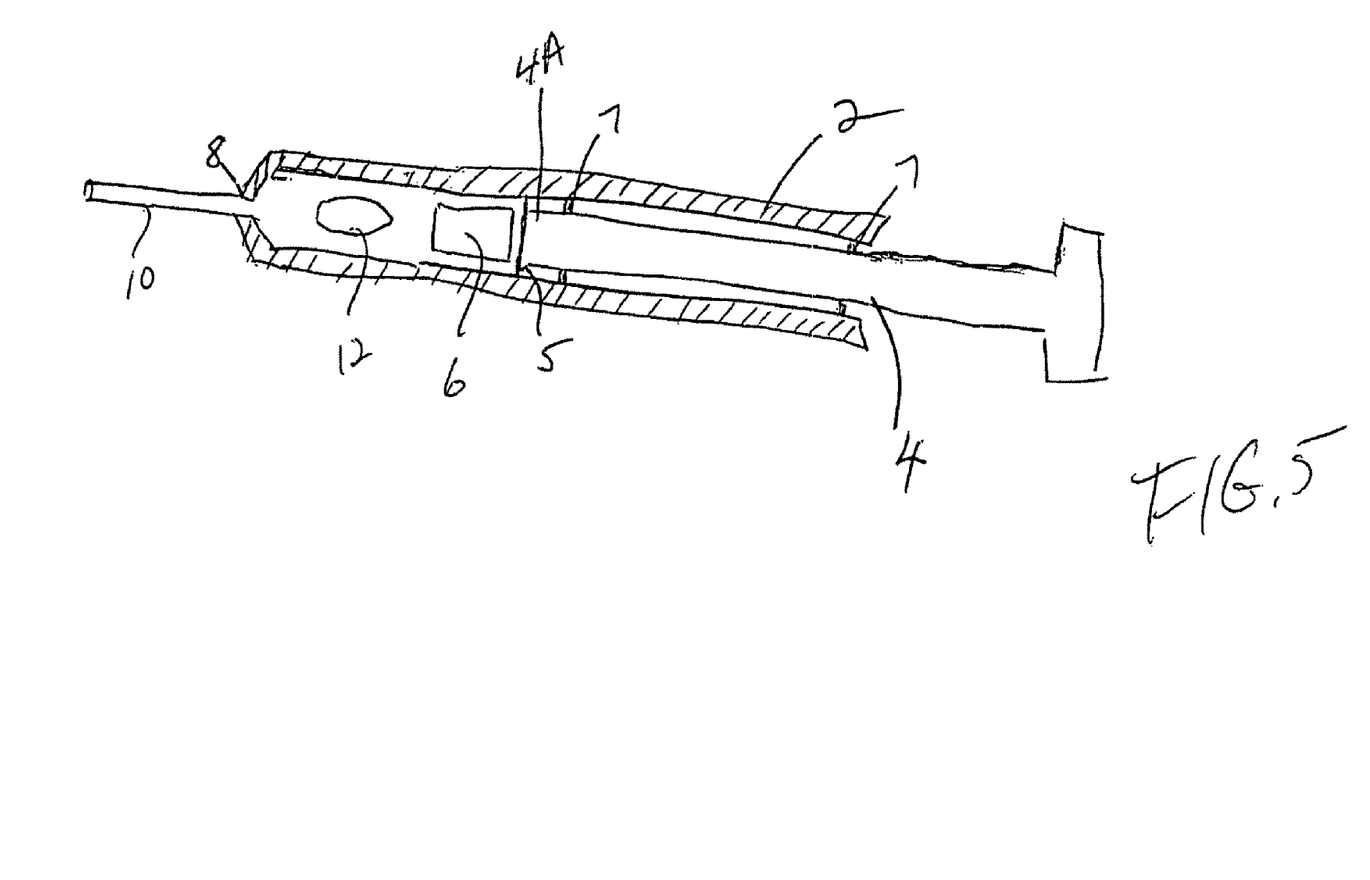
FIG. 5 is a partial cutaway diagram of a syringe that is provided for implanting microparticles that are dispersed from a dispensing device of the invention.

An alternative method uses a syringe, according to FIG. 5 of the present application, that is fitted with a barrel 2 and an ejector 4 which is positioned in barrel 2 by guides 7. The lower end 4A of ejector 4 is adjacent to a sterile frangible vial of an injectable liquid 6. A seal 5 is provided in the barrel 2 at the lower end of ejector 4 to prevent backflow of any liquid when the ejector is depressed to contact a frangible sterile container 6 which when broken by the action of ejector element 4 allows an injectable liquid such as water for injection, normal saline, ringers solution etc. to contact the dispensing device 12 and disperse it into microparticles so that when additional pressure is placed on the main ejector 4 in the main barrel 2 the dispersed microspheres are extruded from the wide gauge needle 10 that is mounted on barrel 2.

Generally, the thickness of the dispensing device for implantation should be from about 0.25 to 2.5 mm whether in the form of a disc, rod or pellet. The dispensing device in the form of e.g. a disk, should have an area equal to a circle having a diameter of about 3 to 10 mm although smaller or larger devices may be made according to the invention. A rod or cylinder shaped dosage form may be sized to be approximately 1 mm in diameter by 3 mm in length The density of the dispensing device increases as the amount of compression force is increased. The density should be sufficiently high that it reduces the rate of release of a compressed sample that is compressed using pressures of 150-600 psi as compared to an uncompressed sample. The hyper-compression step also allows for packing more particles into a finite volume thereby increasing drug loading and will influence the rate of drug release due to the increased density of the compressed dosage form.

Figure 6A:
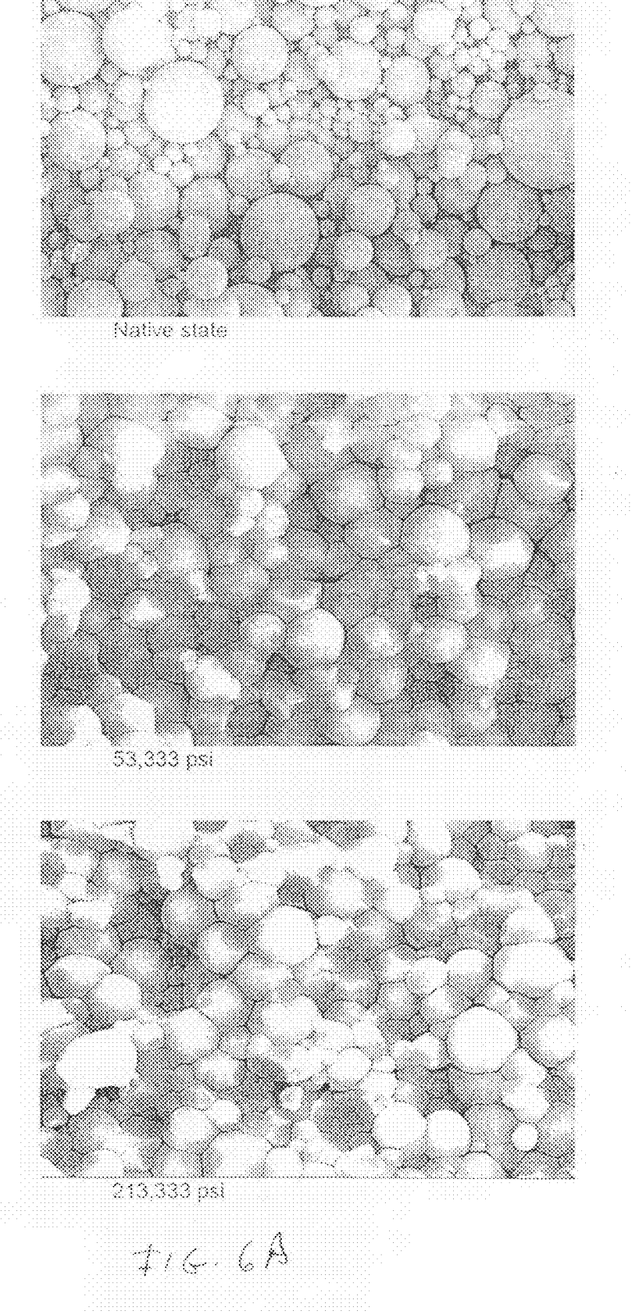
FIGS. 6A and 6B are a series of photomicrorgraphs which show the effect of increasing pressure on compressed microparticles.
Figure 6B:
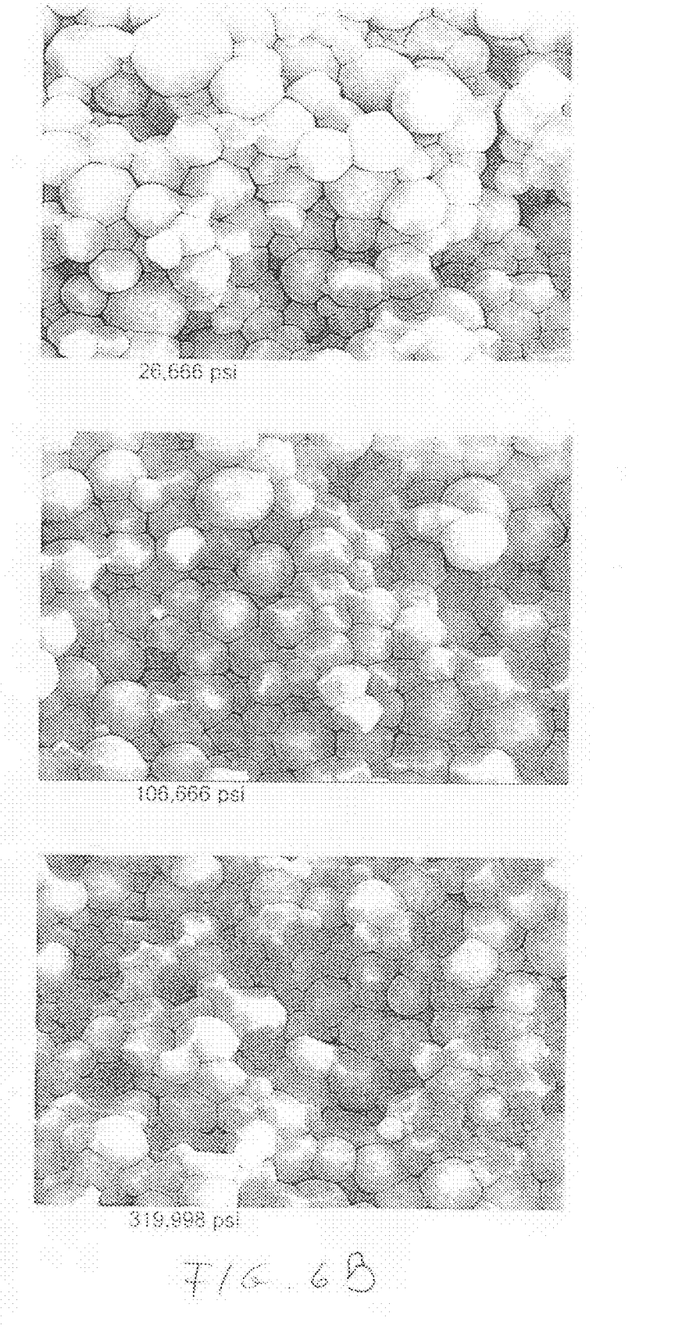

FIGS. 6A and B are a series of six photomicrographs of polylactic acid microspheres containing 20 wt % of dexamethasone prepared according to the general procedure of Example 1. The increasing pressures show that the microspheres begin to show slight deformation and shape distortion after being subjected to 26,666 psi. As observed, the greater the pressure applied the smaller the particle size, the greater the particle distortion and minimizing of spacing between particles. The reduction in particle size is accompanied by an increase in density and higher drug loading per unit of volume.

The invention also includes dispensing devices which have two or more drugs formed into microparticles or nanoparticles with a polymer in order to provide controlled release of drugs intended for combination therapy.

A patch containing the hyper-compressed microparticles or nanoparticles of the invention will have the typical dimensions of transdermal patches that are commercially available.

Where complete surgical removal of a neoplasm is not possible, or where further medication is prescribed, the implantation or placement of the hyper-compressed delivery device may be applied at the site of therapy, to allow for the continuous release of drug, such as 5-fluorouracil, or taxol. The implantation may take place with or without surgical intervention, or it may be implanted or positioned in the course of a surgical procedure where it is not possible to completely remove all affected tissues using an appropriate injector as described herein. The implantation of the hyper-compressed particles of the invention will reduce or avoid the severe systemic side effects of chemotherapy which may cause serious side effects, including damage to healthy skin, and mucosa lining the oral, pharyngeal, esophageal and gastrointestinal tracts. For example, the severe, dose-limiting, painfully debilitating side effect of oral and gastromucositis, resulting from direct contact of the drug when taken orally, or from intravenous administration will be reduced or eliminated. The dose of the drug will depend on the size and location of the neoplasm but generally the implanted dose will be from 0.5-5% or more preferably 1-2% of the systemic dose and will depend on the response of particular neoplasms, the age and condition of the patient, the nature of the pathology as well as any prior therapy. In the case of carmustine which is used alone or in combination with other anti-cancer drugs for local implantation for the treatment of glial tumors, a dose of 5-10 mg may be used by implantation once every 2 to 4 weeks and 5-fluorouracil may be used for pancreatic cancers by the implantation every 2 to 4 weeks of a dispensing device in the affected area which has from 1-2 mg of 5-fluorouracil. Procarbezine may be used in the dispensing device of the invention at a level of 2-4 mg for treating gliomas every 2 to 4 weeks by implantation.

Implants, according to the invention, may be used to deliver analgesic/anti-inflammatory drugs such as indomethacin or other NSAIDs such as aspirin, naproxen, ibuprofen, and the like directly to the tissues surrounding joints. With the adverse event profiles of oral NSAID's and COX-2 inhibitors, this offers the potential of greater efficacy than oral treatments, while potentially reducing the side effects associated with circulating levels of these drugs. When a joint is treated with an anti-inflammatory drug such as triamcinolone, the dose may be 20 to 40 mg with or without 2-4 mg of dexamethasone in the hyper-compressed microcapsules.

Example 1

A dosage formulation of dexamethasone as a compressed microcapsule formulation is prepared by dispersing 325 mg of dexamethasone in 5 g of a poly(dl-lactide) polymer (PLA) (intrinsic viscosity 0.66-0.80 dl/g as measured in a Ubbeholde viscometer by assessing the flow time of polymer solutions; PLA is soluble in acetone, chloroform or dichloromethane) dissolved in 125 ml of chloroform and 3.5 ml of ethanol. The suspension is agitated between 1500 to 2000 RPM with 700 ml of a 2% polyvinyl alcohol (30K to 70K MW) maintained at 4° C. After 6 hours of stirring, the agitating speed is reduced to 700 RPM and chloroform is allowed to evaporate over night. The microspheres formed are recovered by centrifugation at 1500 RPM, washed 3 times with water and lyophilized. The microspheres form a free flowing powder having 6.5 wt % of dexamethasone with the microspheres having a general diameter in the range of 5 to 25 microns. Thereafter, 250 mg of the microspheres are placed in 7.87 mm diameter molds. The molds (upper and lower punches) were placed in an MTS compression strength testing machine, used to measure mechanical compressive strength and material properties on steel specimens, rocks, etc. The machine is capable of providing over 500 kN axial/compression forces when mechanical jaws are used. The machine was modified to accept Carver type upper and lower flat faced stainless steel tablet dies made of premium S7 steel having a 0.3125" internal diameter and 1.1875" outside diameter and an overall length of 1.750". The die's lower punch sits inside the setting ring and the tip stem shortened to 5/16" to minimize torque. An upper sleeve is designed to keep the upper punch straight, allowing it to withstand hyper-compressive forces within which the delivery system is placed.

Figure 4:
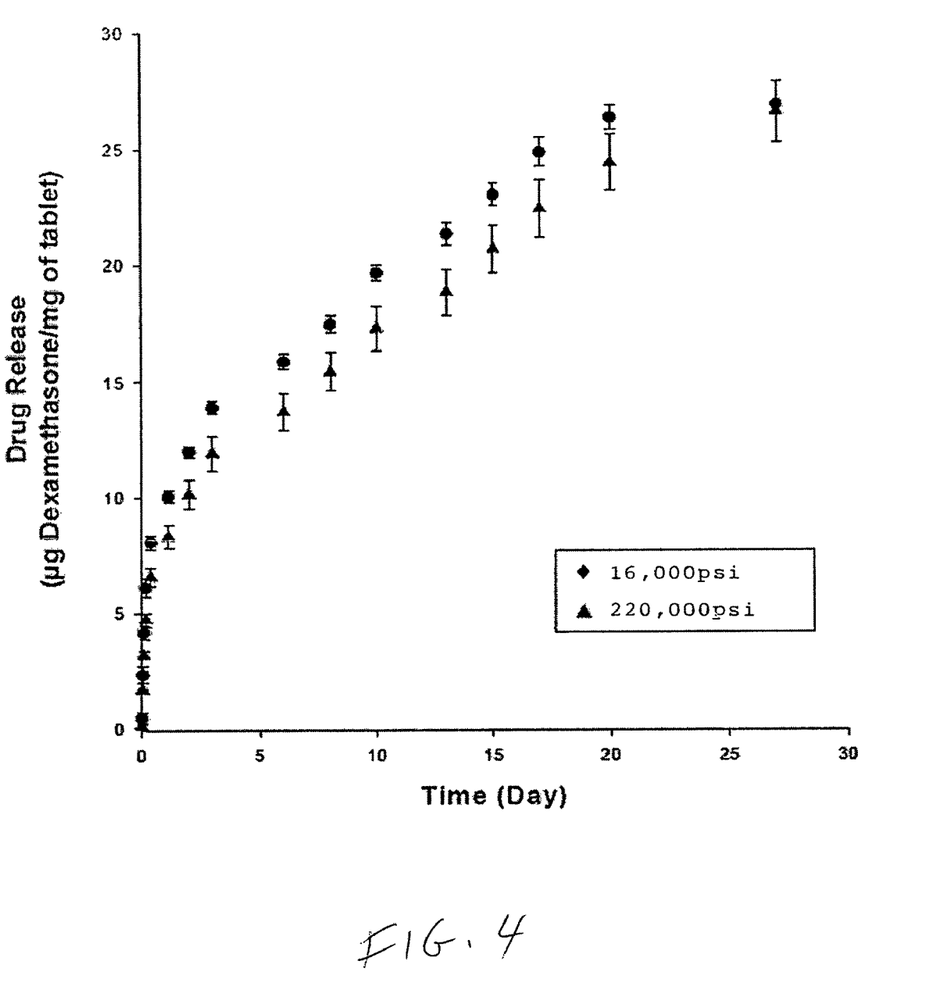
FIG. 4 is a graph which shows the rate of in vitro release of dexamethasone from microspheres of the invention.

In order to avoid excess compression generated heat buildup lest destruction of the microspheres and their medication contents, an incremental pressurization approach is adopted to produce hyper-compressed pellets. Incremental pressurization also reduced the risk of hardware fracture under high pressure, by allowing the metal hardware to adapt to build-up of stress/strain during compression. Using the 7.87 mm mold, hypercompression is applied by increasing the pressure to about 7400 pounds of force or about 100,000 psi. The psi is determined by taking the force applied to the top surface of the dosage form, determining the area of the top surface in square inches and extrapolating the force in pounds applied to pounds per one square inch of top surface area. An additional 5-10 minutes is afforded between further applications of pressure up to a total of about 150,000 psi or about 11,300 pounds of force; thereafter, each increment is set at a more moderate magnitude until about 200,000 psi or about 15,000 pounds of force is applied. Some material yielding is observed while all the hardware is held steady on the MTS tester. For comparison, low compression of microspheres at 1200 pounds of pressure or 16,000 psi was applied. The heights of the pellets, after compression at about 16,000 psi. and at about 220,000 psi of pressure were 5.8 mm and 4.2 mm, respectively; with a density of 1.06 and 1.55 mg/mm2, respectively. Therefore, in an equal volume, the dosage form prepared with about 200,000 psi of compression could hold about 40% more material (by weight) than the dosage form prepared with about 16,000 psi. The dispensing devices prepared using pressures of about 16,000 psi and about 220,000 psi were both placed in 10 ml of a buffer solution of pH 7.4 PBS. The disc made with about 16,000 psi of pressure rapidly disintegrates and disperses compared to its hyper-compressed counterpart. The cumulative in vitro release of dexamethasone from both discs are measured over a 24 hour period of time by placing each disc in individual containers filled with pH 7.4 PBS. The containers were placed on an orbital shaker (at ambient temperature) rotating at 100 RPM. At pre-determined time-points, samples were withdrawn and the containers were replenished with fresh aliquots of PBS and the amounts of dexamethasone released were. The results depicted in FIG. 4 show a very moderate initial burst release of dexamethasone which becomes a pseudo-first order release after one day. The disc that is made with low compression (about 16,000 psi) showed about 20% faster release than the hyper-compressed pellet during this test.

Example 2

A cylindrical shaped dosage form is made using dexamethasone and the polymer system was prepared as described above. The dosage form measures 7.87 mm in diameter, has a thickness of 1 mm, a weight of 60 mg and a drug loading of 6.5%. The same 7.87 mm diameter mold was filled with 60 mg of DSP Dexamethasone, with a comparable incremental pressurization approach was used by applying a compression pressure of 211,685 psi. The dosage form is placed beneath the conjunctiva in the super temporal quadrant of the eyes of five pigs. The level of dexamethasone in the aqueous humor and the vitreous humor is determined at 0.25 day, 1 day, 3 days, 7 days and 14 days by sampling and analyzing the vitreous humor and the aqueous humor. The concentrations of dexamethasone are reported in FIG. 3.

Figure 1:
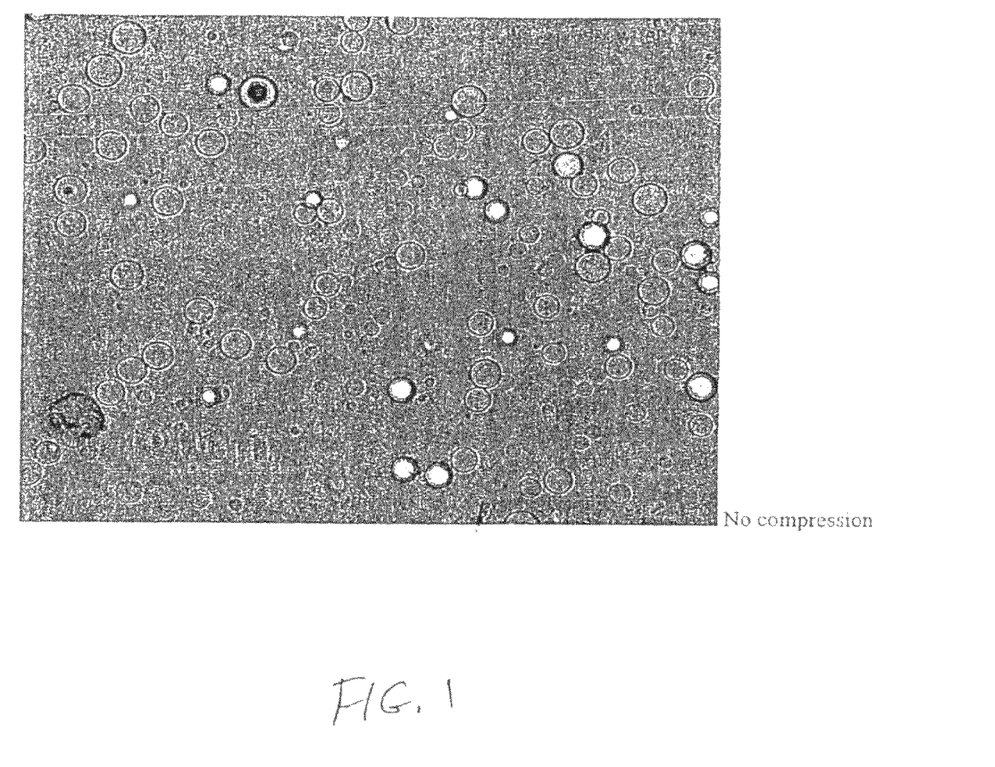
FIG. 1 is a photomicrograph of uncompressed microparticles according to Example 1.
Figure 2:
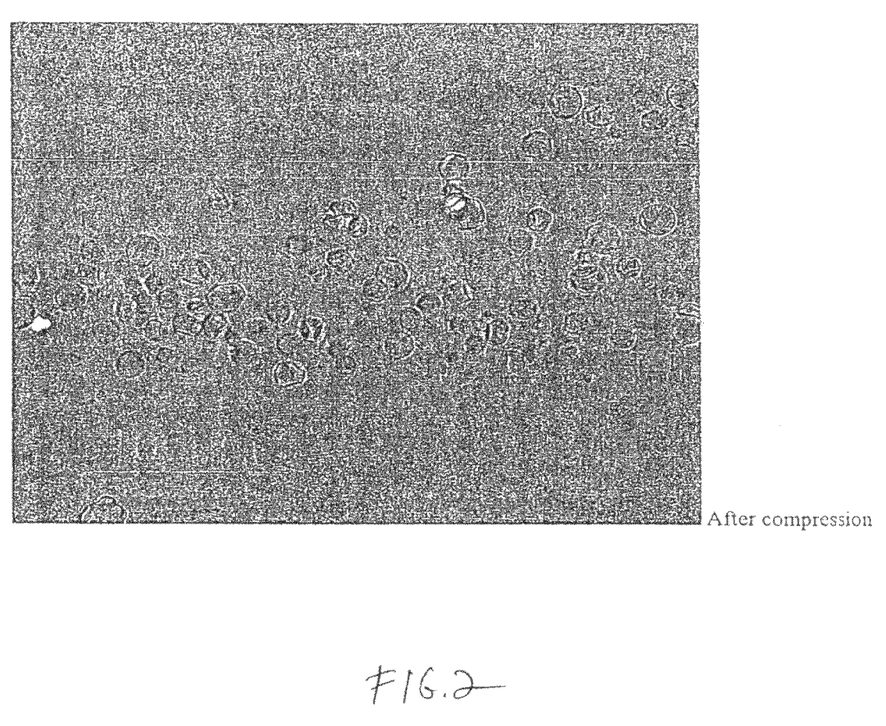
FIG. 2 is a photomicrograph of compressed microparticles according to Example 1.
Figure 3:
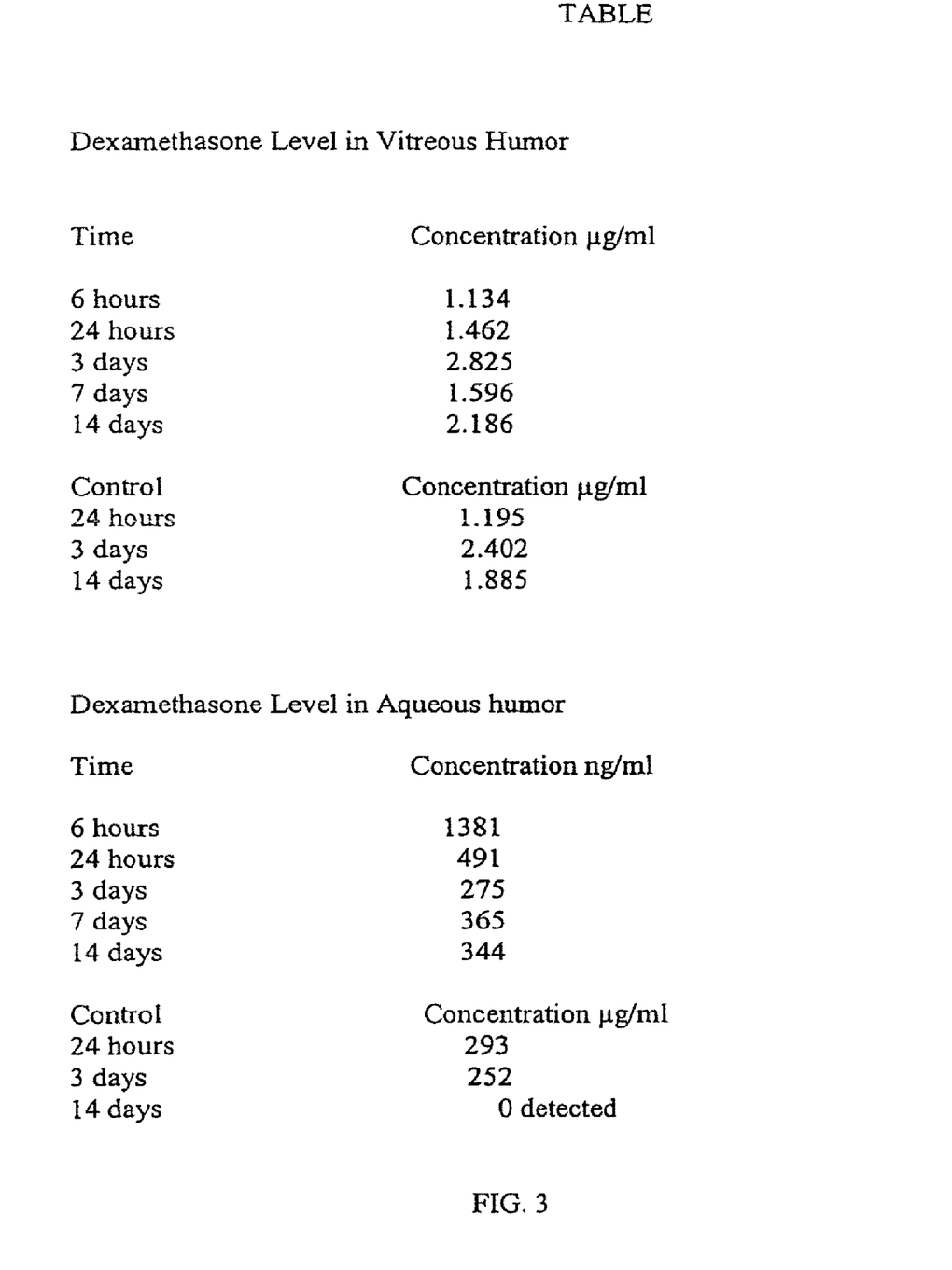
FIG. 3 is a table that reports the level of dexamethasone detected in the vitreous humor and in the aqueous humor as found in example 3.

The release profile shown in FIG. 3 shows that the 211,685 psi of forces disc provided sustained release of dexamethasone for the entire 14 days of the study. Tests of plasma found no detectable dexamethasone which confirmed that the controlled release dosage form has no systemic effect.

Example 3

A study was performed to assess the effects of longer term implantation of cylindrical pellets compressed at 301,568 psi, measuring 5 mm length×3 mm diameter, in rabbit ocular tissues. A new 3-mm diameter mold (prepared and adapted to fit/interchange with the supporting hardware of the 7.87 mm diameter mold) was utilized to prepare the smaller pellets required for the rabbit eye. Due to dimensional considerations and the need to reconcile with the pressure applied for preparing the pellets and the mechanical tolerance of the mold, the incremental pressurization approach, described above was utilized, an initial pressure of 1000 lb was applied; thereafter, ~500 lb of additional pressure was applied approximately every 5 minutes until it reached about 300,000 psi range. The height of the pellets (cylinders) produced were about 5 mm. The pressure noted was 301,568 psi. Similar to the pig model as described above, the pellets were implanted beneath the conjunctiva in the superotemporal quadrant of the right eyes. At stipulated time-points, the rabbits were euthanized to harvest the ocular tissues. Accordingly, the implant sites were dissected out and the rest of the tissues were further separated into: sclera/conjunctiva, cornea and lens. FIG. 7 depicts the histology (cryosectioned, H&E stained) of an implant site 9 weeks post-op. The presence of Dex-Micro-Vectors at the implant site is indicative of the sustained presence of the SNS Conversion™ pellet. The existence of a minimal amount of macrophages at the implant site suggests a mild inflammatory response, signifying suppression of the inflammatory response by the sustained release of Dexamethasone T-Vectors.

The dexamethasone levels in rabbit ocular tissue is determined after 13 weeks and is reported in nanograms of dexamethasone per mg of tissue in Table 1. The sclera/conjunctiva, cornea and lens are recovered, processed, and extracted. Dexamethasone levels are determined by HPLC assay. Table 1 reports the dexamethasone recovered from the rabbit ocular tissues after 13 weeks of implantation, which is the longest duration for this study series. The long-term presence of dexamethasone is demonstrated.

TABLE 1

| | |
|---|---|
| Right Sclera/Conjunctiva | 415.1 |
| Right Cornea | 40.4 |
| Right Lens | 78.1 |
| Left Sclera/Conjunctiva | 20.3 |
| Left Cornea | N/A |
| Left Lens | 18.3 |

Example 4

Polymeric microspheres/nanospheres with synthetic corticosteroids (e.g., dexamethasone, prednisolone, budesonide) encapsulated could be formulated using conventional in-emulsion-solvent evaporation methods. A dosage formulation of budesonide as a hyper-compressed microcapsule formulation is prepared by dispersing 10 mg budesonide in 990 mg of a poly(dl-lactide) polymer (PLA, intrinsic viscosity 0.66-0.80 dl/g as measured in a Ubbeholde viscometer by assessing the flow time of polymer solutions) PLA is dissolved in 125 ml of chloroform and 3.5 ml of ethanol. The suspension is agitated between 1500 to 2000 RPM with 700 ml of a 2% polyvinyl alcohol (30 K to 70 K MW) maintained at 4° C. in a suitable apparatus. After 6 hours of stirring, the agitating speed is reduced to 700 RPM and chloroform is allowed to evaporate over night. The microspheres formed are recovered by centrifugation at 1500 RPM, washed 3 times with water and lyophilized. The microspheres form a free flowing powder having 6.5 wt % of budesonide with the microspheres having a general diameter in the range of 5 to 25 microns. Thereafter, 250 mg of the microspheres are placed in 7.87 mm diameter stainless steel die, in a MTS mechanical tester modified for compression (as described in Example 1). A compression force of 211,685 psi is used to form a dispensing device which contains 2.5 mg of butesonide. The thickness (height) of pellets formed is approximately 4.2 mm with a density of about 1.55. The dispensing device prepared is placed in water and disintegrated and dispersed. These pellets are recovered from the dispersing medium and are re-dispersed in water, snap frozen and lyophilized to remove their water content. The particles/particulates recovered are highly compact as compared to the microspheres/nanospheres prepared originally and prior to compression. Consequently, the drug content per finite volume is considerably higher than their counterparts not previously subjected to compression. Moreover, the higher densities of these post-hyper-compressed microspheres/nanospheres render them less susceptible to aggregation and enable them to carry greater momentum to penetrate deeper into the respiratory system upon being mechanically propelled with an inhaler. An amount of the powder (20 mg) containing 200 mcg of butesonide is then conventionally loaded into a pre-metered, pre-filled pulmonary dose of a dry powder inhaler (DPI's).

No large particle sized excipient carriers, such as lactose is added, (or much less needed) to a DPI formulation to improve the inherent problem associated with highly cohesive fine particles: poor flow during capsule filling and metering, emptying, enhancing power stability, and poor aerosolization behavior resulting from the difficulties associated with deagglomeration Example 5

Polymeric nanospheres with nicotine encapsulated could be formulated using conventional in-emulsion-solvent evaporation methods. The dosage formulation of nicotine as a hyper-compressed microcapsule formulation is prepared by first co-dissolving 100 mg. of nicotine with 900 mg of poly (dl-lactide) polymer (PLA, intrinsic viscosity 0.66-0.80 dl/g, as measured in a Ubbeholde viscometer by assessing the flow time of polymer solutions) in 50 ml of chloroform. The nicotine/PLA solution is dispersed into 200 ml of a 4% polyvinyl alcohol (30K to 70K MW) solution. The nicotine/PLA/chloroform solution is dispersed in the PVA solution by sonication (with a probe ultra-sonicator) while maintained at 4° C.; a nanoemulsion is produced after 15 minutes of sonication. This nanoemulsion is agitated by an impeller rotating at 700 RPM overnight to allow chloroform to evaporate. The nanospheres formed are less than 500 nanometers in size, and are recovered by high-speed centrifugation, washed 3 times and lyophilized. These nanospheres also form a free flowing powdery bulk material and could be hyper-compressed to form pellets.

Thereafter, 250 mg of the microspheres are placed in a 10 mm×10 mm square "porate" modified stainless steel mold, with the channels placed in the lower mold, one millimeter apart (100 porates). A compression force of 200K psi is used to form a dispensing device which contains up to 25 mg of nicotine. When the polymer and active are hyper-compressed (as described in Ex. 1), the resulting particles are forced into the channeled lower mold, resulting in pyramidal, or cone 'porate' shapes descending from the tablet body. The porates and the body of the dispensing devise contain the active ingredient(s). The term 'porate' is used to describe pyramidal or cone shaped structures that have a diameter at a superior or largest end of 0.5 mm, and narrowing to an apical point, over a length of 0.1 to 0.5 mm, to create a sharp pointed tip which allows for easy penetration of the skin. The apical or dermal end has a dimension similar to a 30 gauge needle, with a length of 0.1 to 0.5 mm mm to aid the active agent to gain access through the stratum corneum to the interdermal tissues for greater access to the blood vessels for systemic circulation. The square dispensing device is placed on the adhesive part of the patch, with the porates facing the skin, and covered with a protective liner to protect the porates from being exposed. The patient removes the protective liner, composed of polyester fabric, similar to a Band-Aid, and applies moderate thumb pressure to allow the active "porates" on the adhesive layer to penetrate the outer surface of the skin. The active can be dispensed for a period of hours or days before the patch is replaced. Once within the interstitial tissue the drug forms a reservoir from which it slowly disintegrates, released and dispersed into the capillaries and larger blood vessels of the connective tissue.

Example 6

Solid dose micro and nano-particle tablet formation containing polymeric microspheres/nanospheres with insulin encapsulated are advanced as a treatment alternative for injectable insulin. Such an alternative may be especially useful for individuals with immunological-based reactions to repeated injections and who require a temporary recess from daily injections. Solid dose delivery also provides rapid absorption and has the advantage of being painless.

Micro and nano-particle tablets are formulated by first using conventional in-emulsion-solvent evaporation methods. A dosage formulation of insulin as a hyper-compressed microcapsule formulation is prepared by first dissolving 10 mg of insulin in 10 ml of water. This aqueous insulin solution is dispersed in 100 ml of PLA solution (50 mg of PLA dissolved in 100 ml of chloroform), maintained at 4° C. under ultra-sonication (with a probe sonicator) for 30 seconds to form a primary water-in-oil nanoemulsion. Under vigorous agitation (by a handheld homogenizer), the primary nanoemulsion is gradually dispersed in 600 ml of a 2% PVA solution (30K to 70K MW), maintained at 4° C. to form a water-in-oil-in-water secondary emulsion. The homogenizer agitation is terminated after 5 minutes, following which the agitation of this nanoemulsion will be continued by an impeller rotating at 1000 RPM overnight to allow chloroform to evaporate. The nanospheres formed are recovered by high-speed centrifugation, washed 3 times and lyophilized. These nanospheres form a free flowing powdery bulk material which is then placed under hyper-compressed conditions to form oval shaped tablets (punch size, 17.5 mm×10.2 mm), of 220K psi using technology as described in Example 1 The tablets are to be swallowed. The tablets are formulated to break up in the digestive tract, in a sustained format, allowing for depot formation in the intestinal tissue continuous dispersion of the drug, rapid insulin absorption and reactive glucose-lowering effect.

The invention claimed is:

1. A dispensing device which comprises a polymer which is combined with a therapeutic agent in the form of micro or nano particles which are hyper-compressed by the application of 150K psi to 600K psi.
to form a controlled release dispensing unit.

2. A dispensing device as defined in claim 1 where the therapeutic agent is selected from the group consisting of steroids, non-steroidal anti-inflammatory drugs, antihistamines, antibiotics, mydriatics, beta-adrenergic antagonists anesthetics, alpha-2-beta adrenergic agonists, mast cell stabilizers, prostaglandin analogues, sympathomimetics, parasympathomimetics, antiproliferative agents, agents to reduce ocular angiogenesis and neovascularization, vasoconstrictors, anti-neoplastic agents, a polynucleotide, or a recombinant protein analog an angiogenic inhibitors and combinations thereof.

3. A dispensing device as defined in claim 1 where the polymer is selected from the group consisting of poly(alpha hydroxy butyric acid), poly(p-dioxanone) poly(l-lactide), poly(dl-lactide), polyglycolide, poly(glycolide-co-lactide), poly(glycolide-co-dl-lactide), a block polymer of polyglycolide, trimethylene carbonate and polyethylene oxide, or a mixture of any of the foregoing.

4. A dispensing device as defined in claim 2 where the polymer is biodegradable.

5. A dispensing device as defined in claim 1 wherein the microcapsule has been compressed by the application of 200K psi to 400K psi.

6. A dispensing device as defined in claim 1 wherein the microcapsule which has been compressed by the application of 220 psi.

7. A dispensing device as defined in claim 6 where the therapeutic agent is a steroid.

8. A method of locally administering a drug which comprises forming a dispensing device comprising a polymer in combination with a therapeutic agent in the form of a microparticle or nanoparticle which is hyper-compressed by the application of 150K psi to 600K psi to form a controlled release dispensing unit and thereafter placing said dispensing unit in a patient in a location that will provide for the localized or systemic release of the drug.

9. A method as defined in claim 8 where the therapeutic agent is selected from the group consisting of: steroids, non-steroidal anti-inflammatory drugs, antihistamines, antibiotics, mydriatics, beta-adrenergic antagonists, anesthetics, alpha-2-beta adrenergic agonists, mast cell stabilizers, prostaglandin analogues, sympathomimetics, parasympathomimetics, antiproliferative agents, agents to reduce ocular angiogenesis and neovascularization, vasoconstrictors and combinations thereof.

10. A method as defined in claim 9 where the polymer is selected from the group consisting of poly(alpha hydroxy butyric acid), polyp-dioxanone) poly(l-lactide), poly(dl-lactide), polyglycolide, poly(glycolide-co-lactide), polyglycolide-co-dl-lactide), a block polymer of polyglycolide, trimethylene carbonate and polyethylene oxide, or a mixture of any of the foregoing.

11. A method as defined in claim 9 where the polymer and the therapeutic agent are in the form of a rod or other shape ranging in variation of degrees of elongation, circularity, and convexity or surface roughness.

12. A method as defined in claim 11 where the microparticles have been compressed by the application of 200K psi to 400K psi).

13. A method as defined in claim 11 where the therapeutic agent is a steroid.

14. A method as defined in claim 12 where the microparticles have been compressed by the application of 220K psi.

15. A method of locally administering a drug which comprises forming a dispensing device comprising a polymer in combination with a therapeutic agent in the form of a microparticle which is hyper-compressed by the application of 150K psi to 600K psi to form a controlled release dispensing unit and thereafter placing said dispensing unit in contact with an injectable liquid to disperse the microparticles and form a suspension of microparticles prior to placing said suspension in a patient in a location that will provide for release of the drug.

16. A method as defined in claim 15 where the suspension of microparticles is dried and administered by inhalation as a dry dispersion.

17. A transdermal patch which comprises hypercompresssed microparticules or nano particles of a drug and a polymer as defined in claim 1.

18. An oral dosage form which comprises hypercompresssed microparticles or nanoparticles as defined in claim 1.

* * * * *